United States Patent [19]

Raven et al.

[11] Patent Number: 5,624,841
[45] Date of Patent: Apr. 29, 1997

[54] PROCESS FOR THE PRODUCTION OF THERMOPHILIC MICROORGANISMS IN HIGH YIELD

[75] Inventors: Neil D. H. Raven; John D. Cossar; Narendra M. Ladwa; Richard J. Sharp, all of Salisbury, England

[73] Assignee: Microbiological Research Authority, of Centre for Applied Microbiology & Research, Wiltshire, United Kingdom

[21] Appl. No.: 453,083

[22] Filed: May 30, 1995

Related U.S. Application Data

[63] Continuation of Ser. No. 193,107, filed as PCT/GB92/01470, Aug. 7, 1992, published as WO93/03136, Feb. 18, 1993, abandoned.

[30] Foreign Application Priority Data

Aug. 9, 1991 [GB] United Kingdom ............... 9117209

[51] Int. Cl.$^6$ ............................................. C12N 1/20
[52] U.S. Cl. ........................... 435/252; 435/244; 435/804
[58] Field of Search ................................. 435/252.1, 244, 435/804

[56] References Cited

PUBLICATIONS

Bryant, F.O. et al "Characterization of hydrogenase..." The Journal of Biological Chemistry, vol. 264 No. 9, 25 Mar. 1989, Bethesda, US, pp. 5070–5079.

Parameswaran, A.K. et al "Engineering considerations for growth..." Applied Biochemistry and Biotechnology, vol. 18, 1988, Clifton, New Jersey, pp. 53–73.

Blumentals, I.I. et al "The hyperthermophilic archaebacterium pyrococcus..." Annals of the New York Academy of Sciences, vol. 589, 20 May 1990, US, pp. 301–314.

Huber, R. et al "Pyrobaculum gen. nov., a new genus of neutrophilic..." Archives of Microbiology, vol. 149 No. 2, 1987, Springer, Berlin, pp. 95–101.

Patent Abstracts of Japan, vol. 12 No. 209 (C–504) (3056) 15 Jun. 1988 & JP A, 63 7 776 (Anjinomoto Co. Inc.) 13 Jan. 1988. Abstract.

*Primary Examiner*—Irene Marx
*Attorney, Agent, or Firm*—Nixon & Vanderhye

[57] ABSTRACT

A process is described for the growth of anaerobic thermophilic heterotrophic methanogens belonging to the species *Pyrobaculum islandicum* and *Pyrococcus furiosus* to high cell densities under steady state conditions.

14 Claims, 8 Drawing Sheets

PROCESS FOR THE PRODUCTION OF THERMOPHILIC MICROORGANISMS IN HIGH YIELD

This application is a continuation of application Ser. No. 08/193,107, filed Feb. 22, 1994, now abandoned, which was filed under 35 USC 371 as the national phase of PCT/GB92/01470, filed Aug. 7, 1992 published as WO93/03136, Feb. 18, 1993.

This invention relates to a process for the production of thermophilic archaea in high yield.

A remarkable characteristic of the thermophilic archaea is their ability to grow at extremely high temperatures. In nature, these organisms grow in geothermal areas such as terrestrial solfataric springs and mud holes and in marine hydrothermal areas, as well as outflows from geothermal powerplants.

Many workers have realised the potential applications of both thermophilic microorganisms and their thermophilic proteins in industrial processes. Large quantities of microorganisms are consequently required for use in these processes and high yields and reproducible conditions are therefore required. However, the nature of their growth requirements and the sometimes extreme conditions associated therewith present many difficulties in devising procedures achieve these objectives.

The provision of a process for the production of thermophilic archaea on a large scale would therefore be useful in order to study the thermophilic proteins produced and their potential industrial applications.

Many of these organisms obligately evolve hydrogen sulphide as an end product of their metabolism by the reduction of elemental sulphur or some of its compounds (eg sulphite and thiosulphate). Others, however, are capable of evolving hydrogen as an alternative in the absence of elemental sulphur.

As an example of the latter *Pyrococcus is,* a genus of thermophilic bacteria belonging to the archaeal domain and first described by Fiala and Starter in 1986 (Arch. Microbiol, 145: 56–61). *P furiosus* was first isolated from geothermally heated marine sediments and is able to grow in a temperature range between 70° and 103° C. and at pH 5–9 and 0.5–5.0% NaCl. Its optimum growth temperature is 100° C. (Fiala and Starter, supra).

*P furiosus* is a strictly anaerobic heterotroph and grows by a fermentative-type metabolism. The cells are spherical and Gram-negative, being about 0.8 to 2.5 μm in width and possess monopolar polytrichous flagella and a granum-like body visible under light microscopy. Both simple and complex carbohydrates can be utilised, with the production of $CO_2$, $H_2$ and acetate in the absence of elemental sulphur.

In the past, attempts at devising procedures for culturing thermophilic archaea in high yields have resulted in yields no greater than $3\times10^8$ cells/ml (even in the presence of elemental sulphur). In addition, attempts at overcoming problems caused by specific growth requirements or production of hazardous waste products have hindered the production of higher cell densities. $H_2S$ corrosion when sulphur is present in the medium has necessitated the use of expensive $H_2S$-resistant materials for the construction of culture apparatus.

Parameswaran et al, Appl. Biochem. Biotechnol. 18, 53–73 (1988) discloses that *P. furiosus* grows better in the presence of elemental sulphur (reducing the inhibitory effect of $H_2$ on cell growth), but a consequence is that reactor materials are likely to be corroded by the resultant large volume of hydrogen sulfide produced. The reference also discloses that for culture of *P. brocki* lowering $H_2$ partial pressure may reduce $H_2S$ associated problems, but only at the expense of lower cell yields. Modified conventional fermentors, gas lift systems and membrane bioreactors are disclosed as possible bioreactors.

Bryant and Adams (J. Biol. Chem. 1989, vol 264 No 9) disclose a procedure for batch culturing *P. furiosus* in sulphur-free media, sparged with Ar to relieve inhibition by $H_2$. The yields obtained from this procedure were however extremely variable, ranging between 450 and 1100 g (1–3 g/liter) wet weight of cells and cell density of up to $1\times10^8$ ml$^{-1}$ from a 400-liter formenter.

Huber et al (Arch. Microbiol 1987 149:95–101) discloses batch culture of *Pyrobaculum islandicum* (an obligately $H_2S$—evolving thermophilic Archaea). Cell densities of up to $3\times10^8$ ml$^{-1}$ were obtained in stirred $N_2$ sparged cultures in a 300l enamel-protected fermenter using thiosulphate as electron acceptor.

It is thus a disadvantage of the prior art that cultures of Archaea grown on medium free of elemental sulphur can only achieve cell densities of up to $3\times10^8$ ml$^{-1}$ even in batch culture.

It is an object of the present invention to provide a process for the production of thermophilic Archaea which provides higher cell yields. It has now surprisingly been found that high growth yields of thermophilic Archaea in excess of any achieved by prior art processes can be obtained, while operating under steady state conditions.

Thus according to the present invention there is provided a process for continuously producing thermophilic Archaea which comprises growing said Archaea in the presence of a nutrient medium containing assimilable sources of carbon and nitrogen and any necessary complex nutrients required for cell growth, characterised in that the Archaea are grown under steady state conditions, the medium is essentially free of elemental sulphur and an inert gas is continuously introduced into the medium so as to remove hydrogen and/or hydrogen sulphide evolved by the archaea and to enable a cell density $>1\times10^9$ cells/ml to be reached under said steady state conditions.

In a preferred operating mode for the process of the invention, the temperature of the culture is maintained at between 70° and 110° C. For *P. furiosus,* the preferred temperature range is 70° to 103° C., more preferably 80° and 100° C., and most preferably it is maintained at 90° C.

For *P. islandicum* the preferred temperature range is 74° C. to 102° C., more preferably 90° C. to 100° C. and most preferably around 95° C.

It is likewise a preferred feature of the process of the invention that the culture medium in the reactor is maintained at a concentration of ionised salts which effectively mimics the ambient conditions in the natural environment of said thermophilic Archaea.

Thus it is preferred that a suitable concentration of an acceptable salt is maintained in the medium.

Examples of said acceptable salts are the chlorides and bromides of sodium, potassium, magnesium and calcium.

For marine archaea eg *P. furiosus,* it is most preferred that the medium comprises sodium chloride.

It is further preferred that the total salt concentration in the medium is maintained at between 0.1 and 1M, most preferably at 0.5M.

For terrestrial Archaea eg *Pyrobaculum islandicum* it is preferred that the total salt concentration is maintained between 0.001M and 0.1M, most preferably 0.02M.

It is preferred that the inert gas continuously introduced is selected from nitrogen, argon, helium, and sulphur hexafluoride, and it is most preferred that it is nitrogen. The inert gas according to the invention is preferably continuously introduced into the culture medium at a rate of between 0.1 and 1 volume/volume/min$^{-1}$. Most preferably, it is introduced at 0.5 volume/volume/min$^{-1}$. For *P. islandicum* the preferred race is around 0.2 volume/volume/min$^{-1}$.

The reactor most preferably used in the process of the invention is a gas-lift fermenter.

The invention will now be described by way of examples with particular reference to the accompanying drawings in which.

Figure 1:
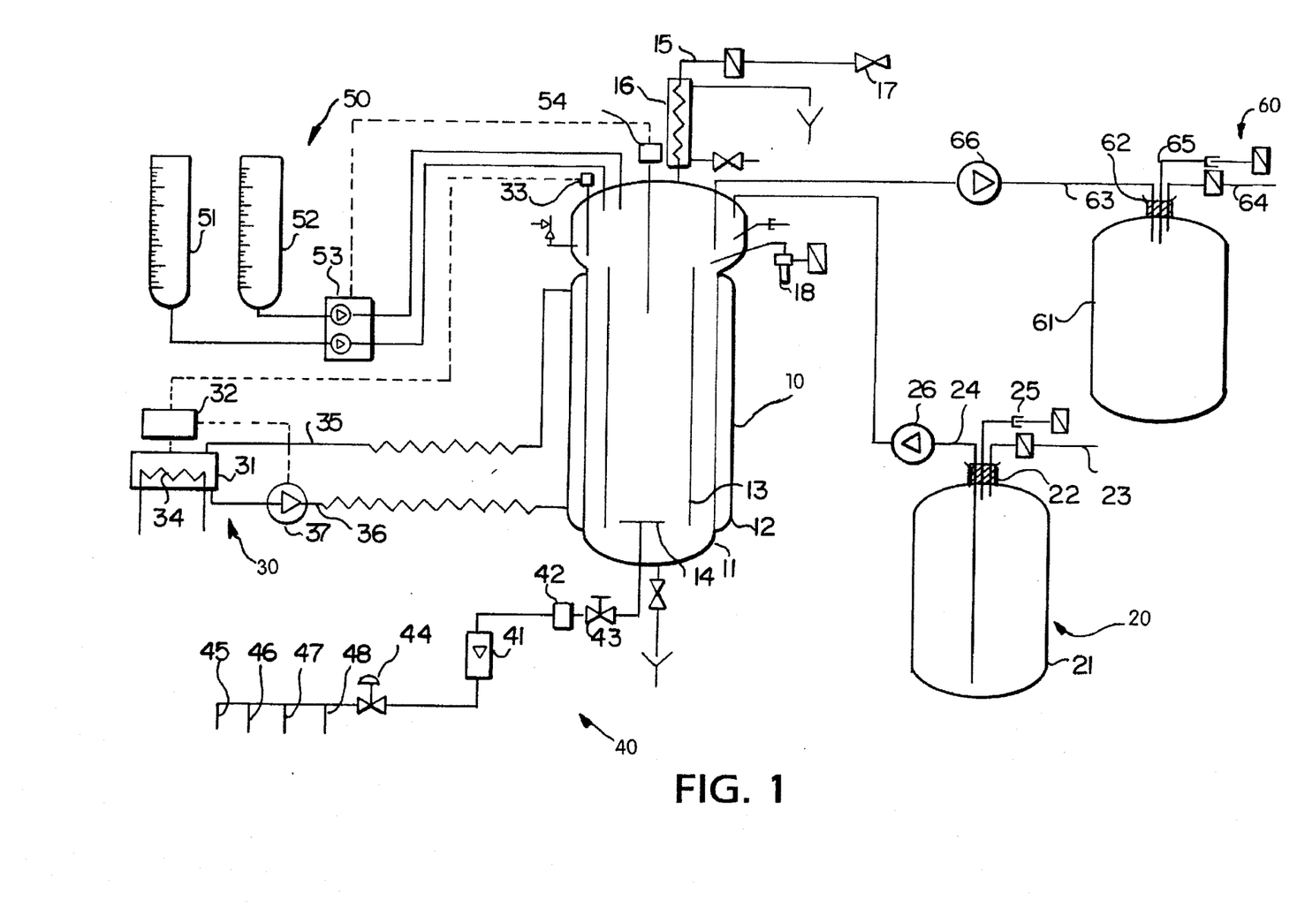
FIG. 1 is a schematic drawing of a continuous culture reactor vessel and ancillary apparatus.

FIG. 1 is a schematic drawing of a continuous culture reactor vessel and ancillary apparatus consisting of gas lift reactor 10, nutrient supply source 20, heating circuitry 30, sparging apparatus 40, pH regulating apparatus 50 and product receiving vessel 60.

The gas lift reactor comprises a cylindrical glass fermentation vessel 11 surrounded by a heating jacket 12. An annular draft tube 13 is located concentrically within the vessel for a purpose to be described below. At the lower end of vessel is located a sintered glass sparger 14, and at the upper end is located a gas outlet 15 provided with a condenser 16 and exhaust 17. A sample valve 18 is also provided at the upper end of vessel.

Nutrient supply source 11 comprises a cylindrical vessel 21 having a narrow opening at one end and which is sealed with a removable bung 22. Said bung is perforated by three holes through which pass an inlet pipe 23, an outlet pipe 24 and a gas balance line 25. The outlet pipe is connected through a pump 26 to the top end of vessel.

The heating circuitry comprises a heater 31 and a temperature control 32 connected in series to a temperature sensor 33 which enters the vessel at the upper end. The heater comprises a heating element 34 and inlet and outlet pipes 35 and 36 connected to the heating jacket 12. The outlet pipe 36 is provided with a pump 37.

The sparging apparatus comprises a flow meter 41, a filter 42 and a needle valve 43, linked in series by pipework to a sintered glass sparger at one end and a regulating valve 44 at the other. Gas sources 45 to 48 are linked by pipework to the regulating valve.

pH regulating apparatus 50 comprises acid and alkali reservoirs 51 and 52, connected by pipework in parallel to the upper end of the vessel. Said pipework runs through a pH control 6 which is linked to a pH sensor at the upper end of the vessel.

Product receiver 60 comprises a cylindrical vessel 61 having a narrow opening at the upper end sealed with a removable bung 62 provided with three holes through which pass an inlet pipe 63, an outlet pipe 64 and a gas balance line 65. The inlet pipe is connected to the upper end of the vessel and is provided with a pump 66.

EXAMPLE 1

*Pyrococcus furiosus* strain Vc 1 (Fiala and Stetter 1986) was obtained from the Deutsch Sammlung von Mikroorganismen und Zellkulturen GmbH as DSM 3638.

Growth Conditions

All growth experiments were performed under anaerobic conditions at 90° C. and pH 7.0.

A modified SME medium (original SME description see Stetter et al (1983) System. Appl. Microbiol) was prepared containing the following:

| | |
|---|---|
| Bacto peptone | 5 g l$^{-1}$ |
| Yeast extract | 1 g l$^{-1}$ |
| Sodium chloride | 28 g l$^{-1}$ |
| Magnesium salts | 10 ml l$^{-1}$ |
| Solution A | 1 ml l$^{-1}$ |
| Solution B | 1 ml l$^{-1}$ |
| Solution C | 1 ml l$^{-1}$ |
| Resazurin (1 mg ml$^1$) | 1 ml l$^{-1}$ |
| Vitamin Solution | 0.5 ml l$^{-1}$ |
| Cysteine HCL | 0.5 g l$^{-1}$ |

| Magnesium salts | gl$^{-1}$ |
|---|---|
| Magnesium sulphate 7H$_2$O | 180 |
| Magnesium chloride 6H$_2$O | 140 |

| Solution A | g l$^{-1}$ |
|---|---|
| Trisodium citrate | 4 |
| Manganese (II) Sulphate 4H$_2$O | 9 |
| Iron (II) Ammonium Sulphate 6H$_2$O | 10 |
| Zinc Sulphate 7H$_2$O | 2.5 |
| Copper (II) Sulphate 5H$_2$O | 0.15 |
| Potassium Aluminium Sulphate 12H$_2$O | 0.3 |
| Cobalt (II) Chloride 6H$_2$O | 0.3 |
| Nickel (II) Chloride | 2.5 |

| Solution B | g l$^{-1}$ |
|---|---|
| Calcium Chloride 2H$_2$O | 56 |
| Potassium Chloride | 16 |
| Strontium Chloride | 4 |

| Solution B | g l⁻¹ |
|---|---|
| Sodium Bromide | 25 |
| Potassium Iodide | 10 |

| Solution C | g l⁻¹ |
|---|---|
| Dipotassium Hydrogen Phosphate | 500 |
| Sodium Tungstate 2H$_2$O | 3.3 |
| Boric Acid | 7.5 |
| Sodium Molybdate 2H$_2$O | 0.15 |
| Sodium Selenite 5H$_2$O | 0.005 |

| Vitamin Solution (modified from Balch et al) | |
|---|---|
| | mg l⁻¹ |
| Biotin | 40 |
| Folic Acid | 40 |
| Pyridoxine-HCL | 200 |
| Thiamine-HCL | 100 |
| Riboflavine | 100 |
| Nicotinic Acid | 100 |
| DL-Calcium Pantothenate | 100 |
| Cyanocobalamin | 2 |
| Lipoic Acid | 100 |

The stock solutions A B and C were prepared as 1000× concentrated solutions and the vitamin solution was prepared at 2000× concentration to be used. The vitamin solution was prepared as a 50% v/v ethanol/water mix. The ethanol soluble components were first dissolved in ethanol and the water soluble components dissolved in water and the solutions mixed. In the event of precipitation, the solution was shaken before use.

The components of the medium described above were mixed in the following order when the medium was prepared:

(1) Sodium Chloride
(2) Magnesium Salts
(3) Solution A
(4) Solution B
(5) Solution C
(6) Resazurin
(7) Vitamin Solution
(8) Bacto Peptone
(9) Yeast Extract
(10) Cysteine-HCL
(11) Sodium Hydroxide When a sulphur-containing medium was required, 30 g l⁻¹ elemental sulphur was added in addition to the above.

Referring to FIG. 1 the medium was sterilised and transferred to vessel 21 by means of inlet pipe 23. The medium in vessel 21 was maintained under anaerobic conditions and unless otherwise stated, anaerobic conditions were maintained throughout the process.

Media was transferred through outlet pipe 24 to the reactor vessel 11 by means of pump 25 at a rate of 400 ml/hr until a volume of 2 liters had been reached.

Figure 2:
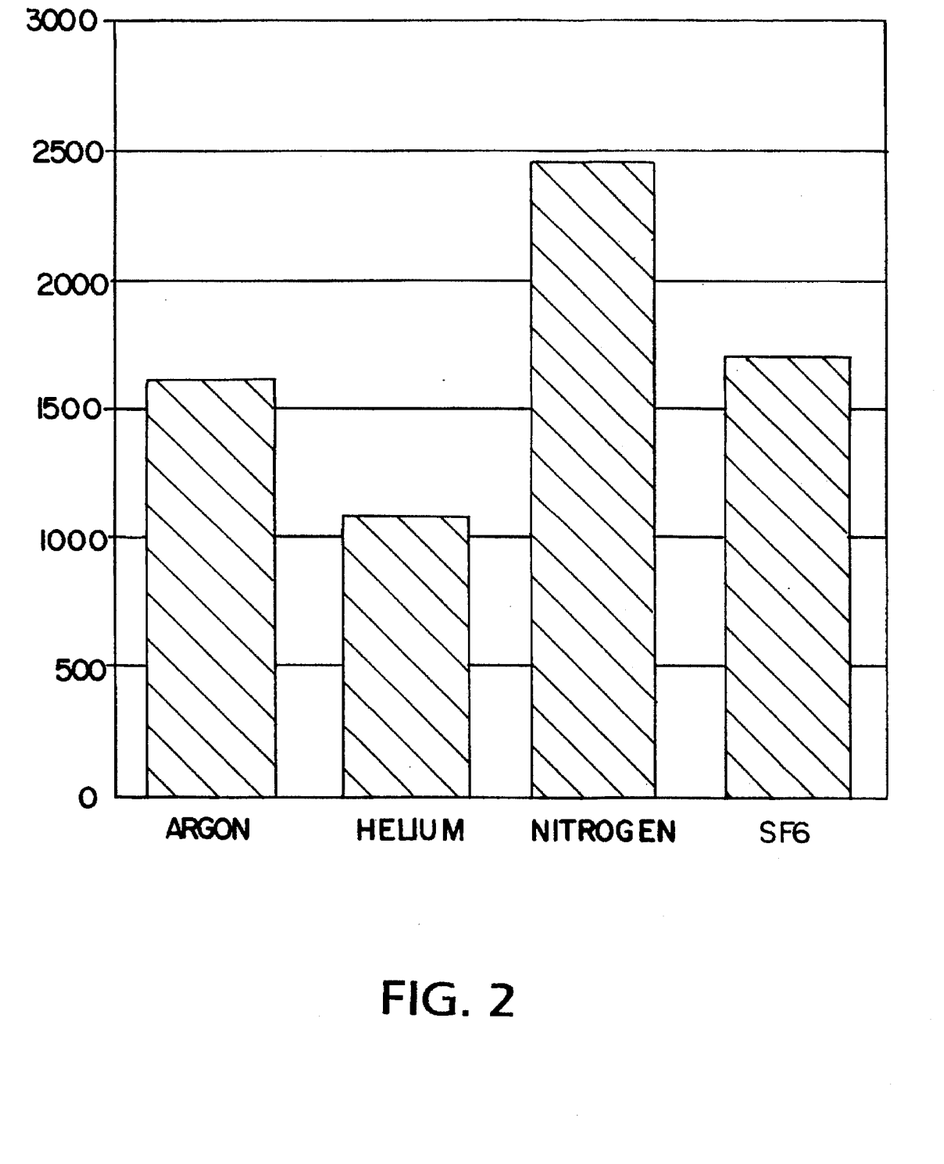
FIG. 2 is a bar chart showing relative cell densities achieved with different sparging gases under equivalent conditions.

The heating circuitry 30 was used to bring the temperature of the medium in vessel 11 up to between 90°–100° C. The temperature was maintained at this level by the temperature control 32. The annular draft tube 13 induces a toroidal circulation of fluid within the vessel 11. Thus bubbles generated by the sparger rise within the riser and gas disengages at the upper end of the vessel. Fermentation medium then returns to the bottom of the vessel flowing downwards in the annular space between the draft tube and the vessel walls. The sparging apparatus was then used to flush the reactor vessel 11 in order to ensure that no traces of oxygen were present, and then a constant flow rate of 0.5 vol/vol/min⁻¹ was established. The gas entered the reactor via the sintered glass sparger 14. The sparging gas used initially was $N_2$. However, He, Ar, or $SF_6$ could also be used for this purpose, or a mixture of all four. When the reactor was run at above 95° C., the pressure in the reactor was adjusted to greater than atmospheric pressure to prevent water loss. A comparison of the efficiency of all four sparging gases was performed and the results are shown in FIG. 2. As will be understood by those skilled in the art, the use of a "gas-lift" reactor of the type described herein facilitates the removal of unwanted gases from the culture whilst providing the necessary mixing which the culture requires for optimum growth. As the thermophilic Archaea are more than usually susceptible to death by shearing forces caused by stirring, this kind of mixing is especially suitable when high cell densities are required.

The medium in vessel 11 was inoculated with a culture of P furiosus strain Vcl obtained from the Deutsche Sammlung Von Microorganismen und Zellkulturen GmbH as DSM 3638 and grown under anaerobic conditions. The rate of flow of the sparging gas was adjusted using the regulating valve until a gas flow of 0.5 vol/vol/min⁻¹ was reached. Cell densities in the reactor were measured by extracting samples from vessel 11 using the sample valve 18.

As the purpose of this process was to achieve the highest cell density possible, all nutrients in the medium were provided in excess in order to avoid any limitation on growth rate. As will be understood by those skilled in the use of continuous culture systems, when no limitation on cell growth is imposed by essential nutrient starvation, the dilution rate in a system can be increased to a point where a maximum cell density and a minimum cell doubling time is achieved. Above this dilution rate cell density decreases due to bacteria being washed from the culture. It was found that cell densities in excess of $3 \times 10^9$ cells ml⁻¹ (=4 g wet/wt l⁻¹) could be maintained indefinitely at a dilution rate of 0.2 hr⁻¹ with a nitrogen flow rate of 0.5 vol/vol/min⁻¹.

RESULTS

Argon as Inert Sparging Gas

Figure 3:
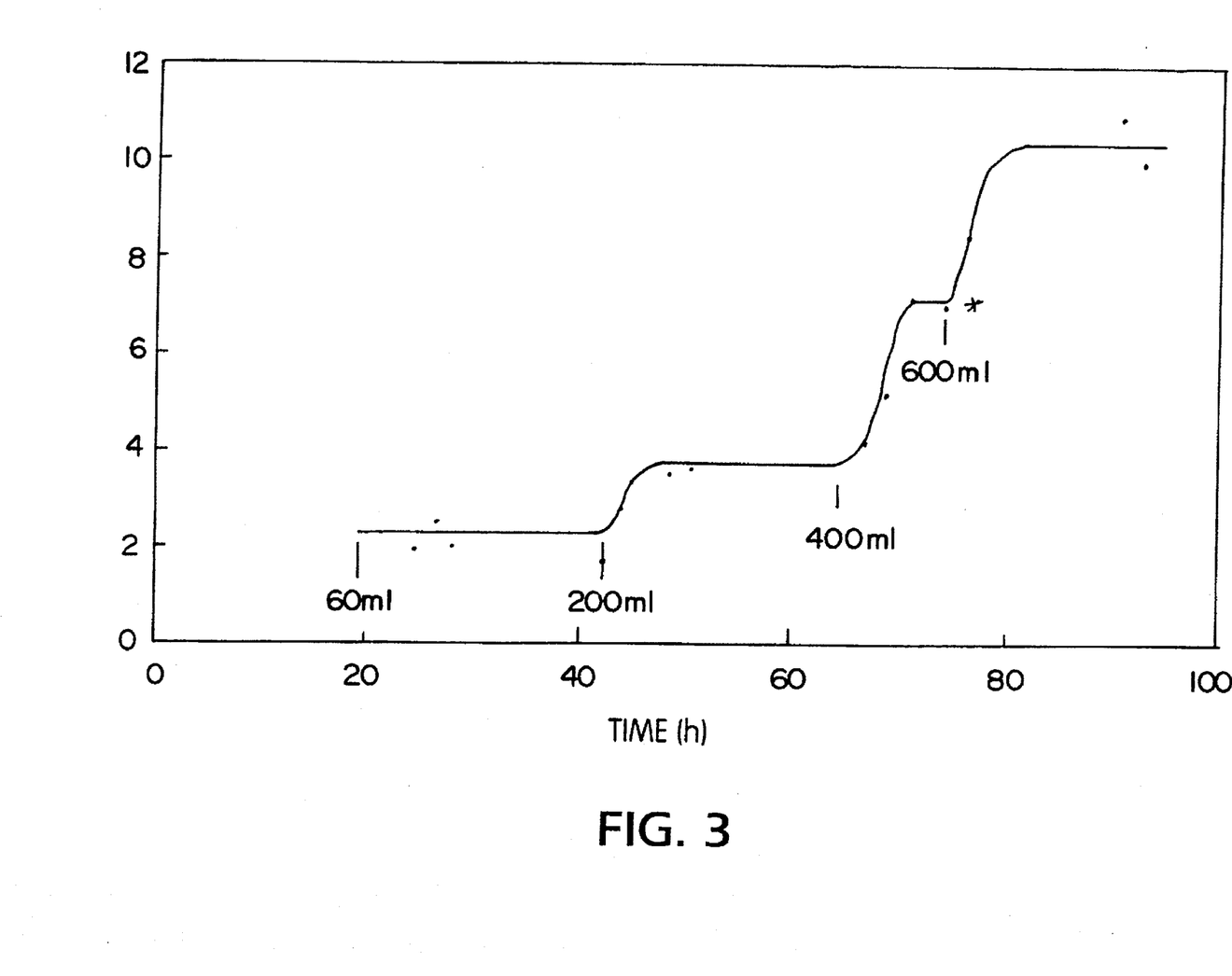
FIG. 3 shows the results of continuous culture of *Pyrococcus furiosus* in the absence of elemental sulphur (90° C., pH7.0, dilution rate 0.2 h$^{-1}$) and the time course of the variation in cell density of a 5 l culture with argon flow rates from 60 ml min$^{-1}$ to 600 ml min$^{-1}$ (0.012–0.12 v v$^{-1}$ min$^{-1}$)
Figure 4:
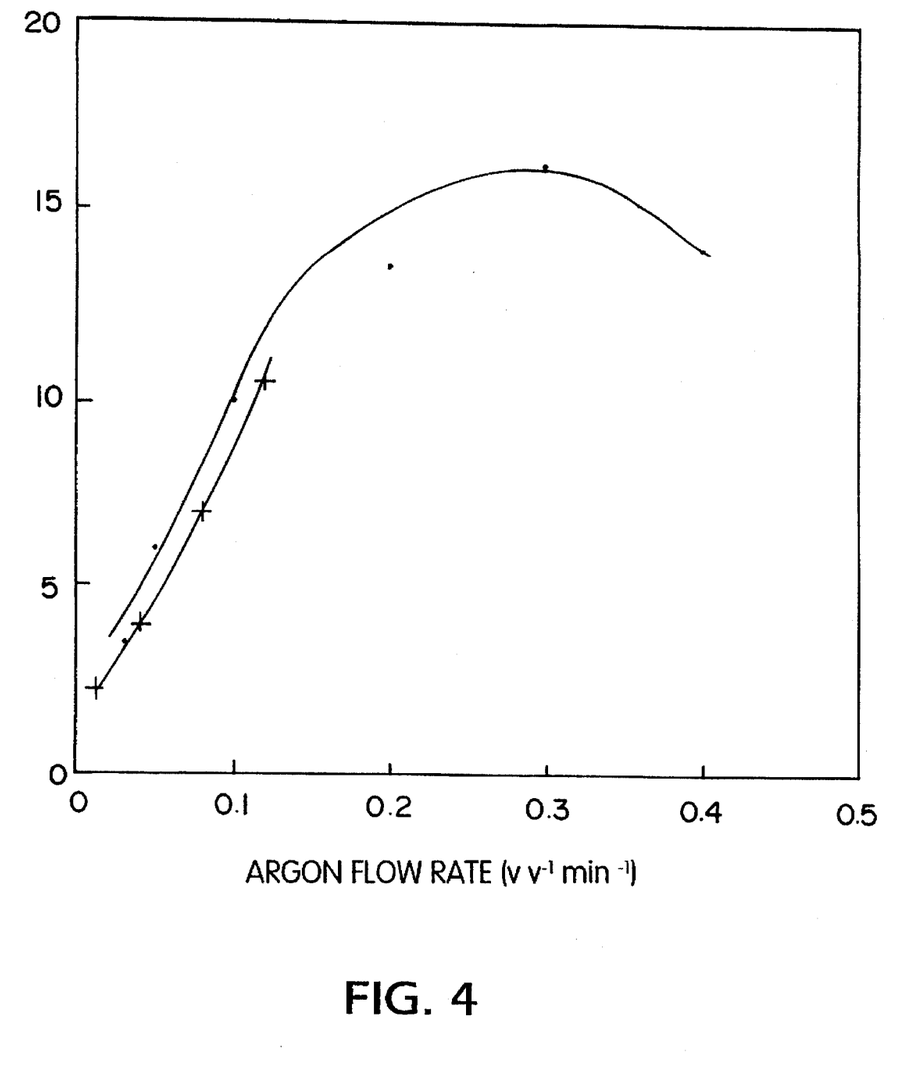
FIG. 4 shows the results of continuous culture of *Pyrococcus furiosus* in the absence of elemental sulphur (90° C., pH7.0, dilution rate 0.2 h$^{-1}$) and the effect of argon flow rate upon equilibrium cell density (bold line—2 l culture, fine line—5 l culture)

Initial experiments on continuous culture of *Pyrococcus furiosus* were performed in a bioreactor with a working volume of 5l at a dilution rate of 0.2 h⁻¹ and argon as the inert sparging gas. Inhibition of growth by hydrogen produced during fermentation had been previously reported to be completely relieved by sparging with argon at 0.02 v v⁻¹ min⁻¹ (Bryant and Adams 1989). In the experimental system described, however, cell densities increased with argon flow throughout the range tested; 0.012–0.12 v v⁻¹ min⁻¹ (FIG. 3). Higher gas flow rates were tested, therefore, at the same dilution rate in a 2l bioreactor of the same design. Steady-state cell densities increased to $1.6 \pm 0.1 \times 10^9$ ml⁻¹ at 0.3 v v⁻¹ min⁻¹, above which level, however, foaming of the medium increased and the equilibrium cell density declined (FIG. 4).

Effect of Alternate Inert Sparging Gases

Figure 5:
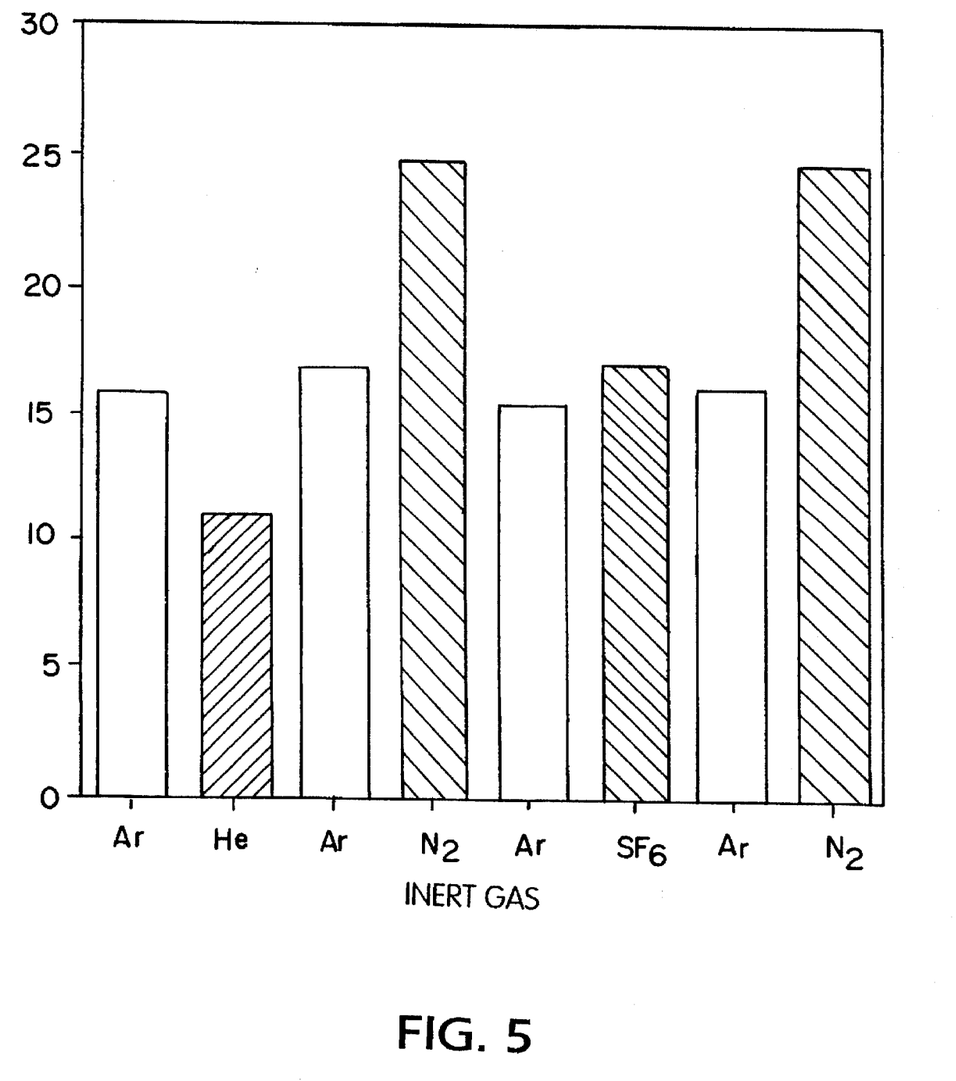
FIG. 5 shows the results of continuous culture of *Pyrococcus furiosus* in the absence of elemental sulphur (90° C., pH7.0, dilution rate 0.2 h$^{-1}$ and the equilibrium cell densities of *Pyrococcus furiosus* with four inert gases, argon (Ar), helium (He), nitrogen (N$_2$) and sulphur hexafluoride (SF$_6$) at a flow rate of 0.3 v v$^{-1}$ min$^{-1}$.

To evaluate whether argon was the optimal inert gas for the system, three other inert gases, helium, nitrogen and sulphur hexafluoride were tested. Al experiments were performed under equivalent conditions with a gas flow rate of 0.3 v v$^{-1}$ min$^{-1}$ and, as previously, a dilution rate of 0.2 h$^{-1}$. The cell density with argon was determined before and after each new gas was supplied. No significant change in this cell density was observed indicating that equivalent culture conditions were present throughout the experiments. Nitrogen was found to support the highest cell densities under these conditions (2.5±0.1×10$^9$ ml$^{-1}$) and to be significantly better than either argon (1.6±0.1×10$^9$ cells ml$^{-1}$). These gases in turn supported significantly higher cell densities than helium (1.1±0.1×10$^9$ cells ml$^{-1}$); (FIG. 5).

Optimisation of Nitrogen Sparging Rate

Figure 6:
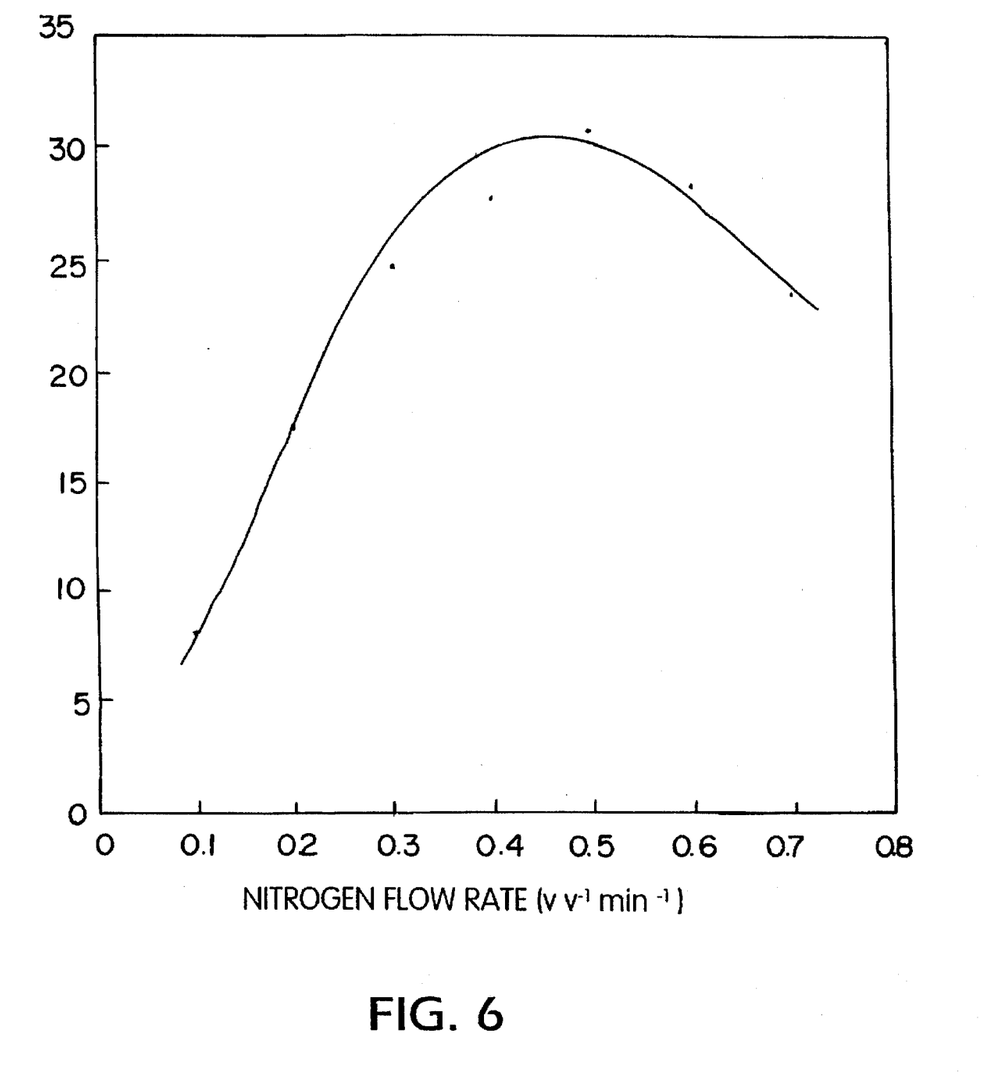
FIG. 6 shows the results of continuous culture of *Pyrococcus furiosus* in the absence of elemental sulphur (90° C., pH7.0, dilution rate 0.2 h$^{-1}$) and the effect of nitrogen flow rate upon eqilibrium cell density.

Nitrogen flow rates from 0.1–0.7 v v$^{-1}$ min$^{-1}$ (in 0.1 v v$^{-1}$ min$^{-1}$ intervals) were tested sequentially to determine the optimum sparging rate. Cell densities were found to increase with nitrogen flow up to 0.5 v v$^{-1}$ min$^{-1}$, where 3.1±0.1×10$^9$ cells ml$^{-1}$ were maintainable at a dilution rage of 0.2 h$^{-1}$. Foaming of the medium and a decline in cell density were observed at 0.6 and 0.7 v v$^{-1}$ min$^{-1}$ (FIG. 6). The optimum nitrogen flow rate of 0.5 v v$^{-1}$ min$^{-1}$ gave a biomass yield of 4.0 g wet weight per liter of culture eluate, giving the bioreactor a productivity of 0.8 g per hour per liter culture volume.

Biomass Production

Figure 7:
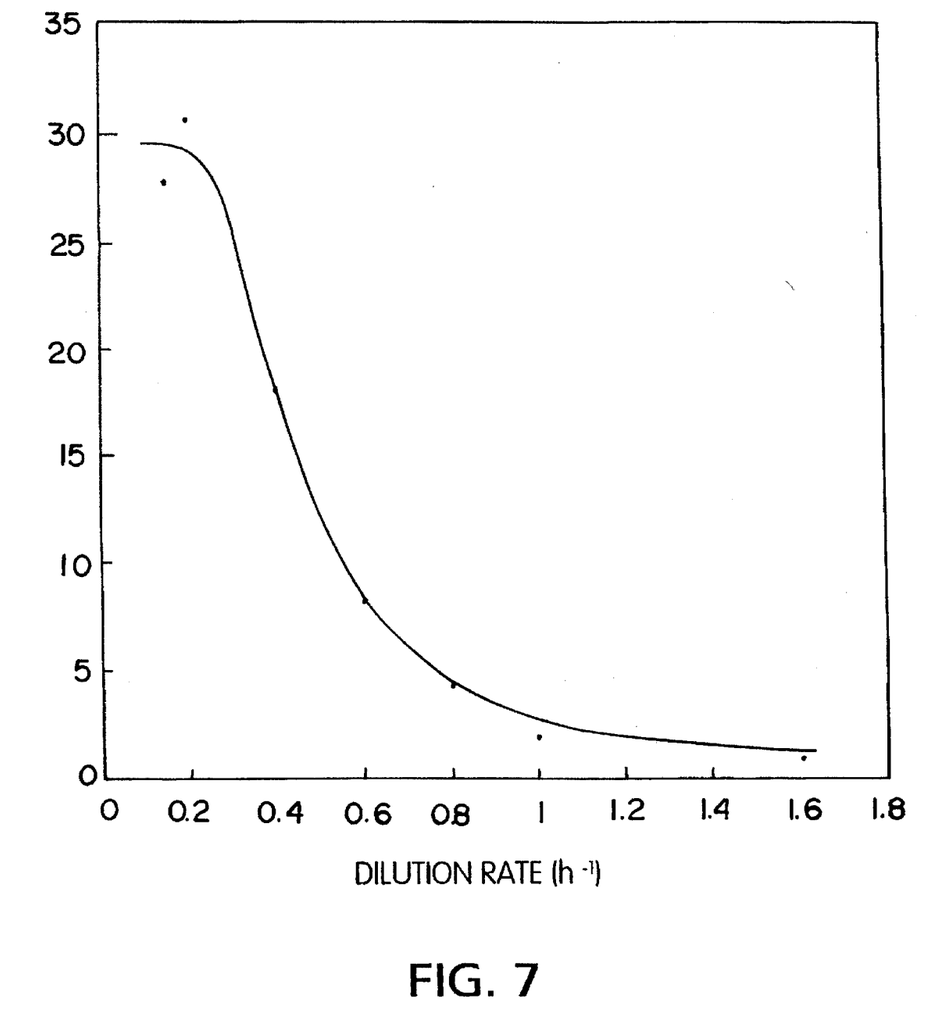
FIG. 7 shows the results of continuous culture of *Pyrococcus furiosus* in the absence of elemental sulphur (90° C., pH7.0, nitrogen flow rate 0.5 v v$^{-1}$ min$^{-1}$). Effect of dilution rate upon equilibrium cell density.

An optimal doubling time at 90° C. of approximately 50 minutes had been previoulsy reported for *Pyrococcus furiosus* (Fiala and Stetter 1986). It was considered, therefore, that the cell densities achieved might be maintainable at dilution rates higher than 0.2 h$^{-1}$, giving an increase in the biomass production rate of the bioreactor. Dilution rates from 0.2–1.6 h$^{-1}$ were tested, however, progressively lower equilibrium cell densities were achieved as the dilution rate was increased (FIG. 7).

Figure 8:
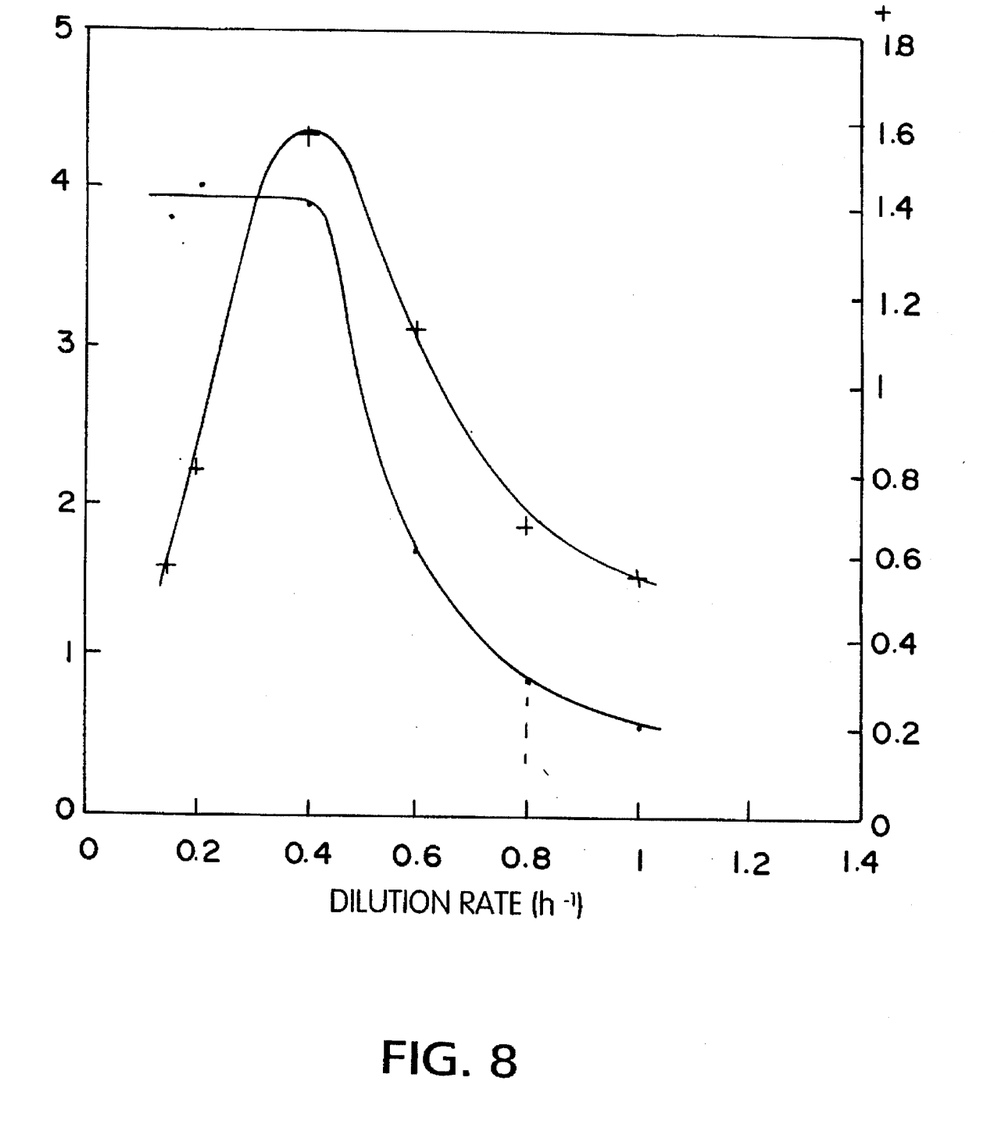
FIG. 8 shows the results of continuous culture of *Pyrococcus furiosus* in the absence of elemental sulphur (90° C., pH7.0, nitrogen flow rate 0.5 v v$^{-1}$ min$^{-1}$) and the effect of dilution rate upon biomass production (bold line—biomass per liter of culture eluate, fine line biomass production per hour per liter of culture volume (2 l)).

Biomass per liter of culture eluate also declined with increasing dilution rate, but the rate of decline was lower (FIG. 8). This correlated well with an apparent increase in cell size observed under the microscope. Total biomass productivity of the bioreactor (biomass per liter of culture eluate×dilution rate) was highest at a dilution rate of 0.4 h$^{-1}$, generating 1.56 g wet weight of cells per hour per itre culture volume (FIG. 8).

EXAMPLE 2

*Pyrococcus furiosus* was grown at a cell density of 10$^{10}$ ml$^{-1}$ (4 g l$^{-1}$ wet weight of cells) when the medium was modified with the peptone (5 g l$^{-1}$) being replaced by maltose (20 mM) and an amino acid cocktail formulated as follows: Glutamate and Glycine, 80 mg l$^{-1}$; Arginine, 60 mg l$^{-1}$; Cysteine and Proline, 50 mg l$^{-1}$; Threonine, Histidine, Isoleucine, Lysine, Leucine and Asparagine, 40 mg l$^{-1}$; Methionine, Phenylalanine, Serine, Alanine, Tryptophan, 30 mg l$^{-1}$ and Valine, Glutamine and Aspartate, 20 mg l$^{-1}$. All other conditions were as in Example 1.

EXAMPLE 3

*Pyrococcus furiosus* was grown at a cell density of 6.6×10$^9$ ml$^{-1}$ (biomass 3.5 gL$^{-1}$) under the conditions of Example 2 when the yeast extract (1 g L$^{-1}$) was omitted.

This represents high cell density growth on a defined medium and compares with 2×10$^7$ ml$^{-1}$ obtained in the only other reports of growth of *Pyroccus furiosus* on a defined medium (Blumentals et al, 1990 and Snowden et al, 1992)

EXAMPLE 4

Using a gas lift fermenter steady state cell densities of 1×10$^9$ ml$^{-1}$ (at 95° C., pH 6.0, dilution rate 0.1 h$^{-1}$ and nitrogen flow rate of 0.2 v v$^{-1}$ min$^{-1}$) were obtained for *Pyrobaculum islandicum*. The growth medium in this case was modified from the basal mineral medium of Allen, 1959 and contained:

Bacto Peptone 0.5 g l$^{-1}$
Yeast Extract 0.2 g l$^{-1}$
1- cysteine 0.5 g l$^{-1}$
Sodium thiosulphate 5 H$_2$O 2 g l$^{-1}$
Sodium tungstate 3.3 mg l$^{-1}$
Boric acid 7.5 mg l$^{-1}$
Sodium molybdate 2 H$_2$O 0.15 mg l$^{-1}$
Sodium selenite 5 H$_2$O 5 µg l$^{-1}$ in addition to the mineral salts of Allen. The pH was adjusted to 6.0 with HCl.

REFERENCES

1. Allen M. B., (1959). Studies with *Cyanidium caldanium* an anomalously pigmented chlorophyte. Arch. Microbiol 32:270–277.
2. Balch W. E., Fox G. E., Magrum L. I., Woese C. R., and Wolfe R. S., (1979). Methariogens: reevaluation of a unique biological group. Microbiol. Rev. 43:260–296.
3. Blumentals I. I., Brown S. H., Schico R. N., Skaja A. K., Costantino H. R. and Kelly R. M. (1990). The hyperthermophilic archaebacterium *Pyrococcus furiosus*. Development of culturing protocols, perspectives on scale up and potential applications. Am. N.Y. Acad. Sci 589:301–314.
4. Bryant F. O., Adams M. W. W (1989), Characterization of hydrogenase from the hyperthermophilic archaebacterium *Pyrococcus furiosus*. *J Biol Chem* 264:5070–5079.
5. Fiala G., Stetter K. O. (1986). *Pyrococcus furiosus* sp. nov. represents a novel genus of marine heterotrophic archaebacteria growing optimally at 100° C. Arch Microbiol 145:55–61
6. Huber R., KristJannson J. K. and Stetter K. O. (1987). Pyrobaculum gen.nov., a new genus of neutrophilic, rod-shaped archaebacteria from continental solfataras growing optimally at 100° C. Arch. Microbiol 149:95–101.
7. Parameswaran A. K., Su W-W., Schicho R. N., Provan C. N., Malik B. and Kelly R. M. (1988). Engineering Considerations for growth of bacteria at temperatures around 100° C. Appl. Biochem. Biotechnol. 18:53–73.
8. Snowden L. J., Blumentals I. I. and Kelly R. M. (1992). Regulation of proteolytic activity in the hyperthermophile *Pyrococcus furiosus*. Appl. Environ. Microbiol. 58:1134–1141.
9. Stetter K. O., Konig H., Stackebrandt E. (1983). Pyrodictium gen. nov., a new genus of submarine disc-shape sulphur reducing archaebacteria growing optimally at 105° C., System Appl. Microbiol 4:535–551.

We claim:

1. A process for continuously growing an anaerobic thermophilic heterotrophic bacterium selected from the group consisting of *Pyrobaculum islandicum* and *Pyrococcus furiosus*, which comprises the steps of:

continuously growing said bacterium in a nutrient medium containing assimilable sources of carbon and nitrogen, wherein the bacterium is grown under steady state conditions, the medium is free of elemental sulfur and an inert gas is continuously introduced into the medium at a rate of between 0.1 and 1 volume/volume/ $min^{-1}$ so as to remove any hydrogen and hydrogen sulfide evolved by the bacterium and wherein a cell density greater than or equal to $1 \times 10^9$ cells per ml is reached under steady state conditions, said process being carried out at a dilution rate of 0.1 to 0.8 $h^{-1}$; and recovering said bacterium from the medium.

2. The process of claim 1, in which the inert gas is continuously introduced into the culture medium at a rate of between 0.20 and 0.75 volume/volume/$min^{-1}$.

3. The process of claim 1, in which the inert gas is continuously introduced into the culture medium at a rate of 0.5 volume/volume/$min^{-1}$.

4. The process of claim 1, wherein the bacterium is grown in a gas-lift fermenter.

5. The process of claim 1, in which the inert gas is selected from nitrogen, argon, helium, and sulfur hexafluoride.

6. The process of claim 5, in which the inert gas is nitrogen.

7. The process of claim 1, wherein the medium comprises ionized salts at a concentration of between 0.1 and 1M.

8. The process of claim 7, in which the concentration of ionised salts in the medium is maintained at 0.5M.

9. The process of claim 1, wherein said process is carried out at a dilution rate of 0.4 $h^{-1}$.

10. The process of claim 1, wherein said process is carried out at a dilution rate of 0.2 $h^{-1}$.

11. The process of claim 1, wherein the medium comprises at least one sulfur compound selected from the group consisting of sulfates and thiosulfates.

12. A process for continuously growing an anaerobic, thermophilic heterotrophic bacterium selected from the group consisting of *Pyrobaculum islandicum* and *Pyrococcus furiosus* to a cell density greater than or equal to $1 \times 10^9$ cells per ml, said process comprising the steps of:

growing said bacterium in a nutrient medium, said medium containing assimilable sources of carbon and nitrogen, said medium being free of elemental sulfur and;

continuously introducing an inert gas selected from a group consisting of nitrogen, argon, helium and sulfur hexafluoride into said medium at a rate of between 0.1 and 1 volume/volume/$min^{-1}$ so as to remove any hydrogen and hydrogen sulfide evolved by said bacterium, said process being carried out at a dilution rate of 0.1 to 0.8 $h^{-1}$; and recovering said bacterium from said medium.

13. The process of claim 12, wherein said process carried out at a dilution rate of 0.4 $h^{-1}$.

14. The process of claim 13 wherein said bacterium is grown in a gas lift fermenter.

* * * * *